United States Patent [19]

Moore et al.

[11] Patent Number: 5,028,240
[45] Date of Patent: Jul. 2, 1991

[54] SEPARATION AND CONCENTRATION OF LOWER ALCOHOLS FROM DILUTE AQUEOUS SOLUTIONS

[75] Inventors: Raymond H. Moore, Richland; David E. Eakin, Kennewick; Eddie G. Baker; Richard T. Hallen, both of Richland, all of Wash.

[73] Assignee: Battelle Memorial Institute, Richland, Wash.

[21] Appl. No.: 469,279

[22] Filed: Jan. 24, 1990

[51] Int. Cl.$^5$ ............................................. C10L 1/02
[52] U.S. Cl. .................................... 44/453; 62/536; 203/14; 203/48; 203/57
[58] Field of Search .................. 44/53, 56, 77, 453; 62/536; 203/52, 57, 48, 14; 209/165

[56] References Cited

U.S. PATENT DOCUMENTS

| | | | |
|---|---|---|---|
| 2,540,083 | 2/1951 | Arnold | 260/666 |
| 3,969,196 | 7/1976 | Zosel | 203/49 |
| 4,251,231 | 2/1981 | Baird | 44/53 |
| 4,297,172 | 10/1981 | Kyle | 44/53 |
| 4,349,415 | 9/1982 | DeFilippi et al. | 203/14 |
| 4,385,914 | 5/1983 | Hewitt et al. | 62/536 |
| 4,425,137 | 1/1984 | Roth | 44/56 |
| 4,437,938 | 3/1984 | Bhise et al. | 203/14 |
| 4,490,153 | 12/1984 | Sze et al. | 44/56 |
| 4,517,298 | 5/1985 | Tedder | 44/56 |
| 4,692,432 | 9/1987 | Tedder | 44/56 |

OTHER PUBLICATIONS

Mehta, G. D. and Fraser, M. D., "A Novel Extraction Process for Separating Ethanol and Water," *Ind. Eng. Chem. Proc. Des. Dev.*, 24:556–560, (1985).
Chowdhury, J., "CPI Warm Up to Freeze Concentration," *Chem. Eng.*, Apr. 25, 1988, pp. 24–31.

*Primary Examiner*—Margaret B. Medley
*Attorney, Agent, or Firm*—Klarquist, Sparkman, Campbell, Leigh & Whinston

[57] ABSTRACT

A process for producing, from a dilute aqueous solution of a lower ($C_1$–$C_5$) alcohol, a concentrated liquid solution of the alcohol in an aromatic organic solvent is disclosed. Most of the water is removed from the dilute aqueous solution of alcohol by chilling sufficiently to form ice crystals. Simultaneously, the remaining liquid is extracted at substantially the same low temperature with a liquid organic solvent that is substantially immiscible in aqueous liquids and has an affinity for the alcohol at that temperature, causing the alcohol to transfer to the organic phase. After separating the organic liquid from the ice crystals, the organic liquid can be distilled to enrich the concentration of alcohol therein. Ethanol so separated from water and concentrated in an organic solvent such as toluene is useful as an anti-knock additive for gasoline.

23 Claims, 2 Drawing Sheets

SEPARATION AND CONCENTRATION OF LOWER ALCOHOLS FROM DILUTE AQUEOUS SOLUTIONS

FIELD OF THE INVENTION

The present invention relates to a process for extracting and concentrating a lower ($C_1$–$C_5$) alcohol from dilute aqueous solutions. In one specific embodiment, this invention relates to a process for producing a concentrated solution of ethyl alcohol in an organic solvent suitable for use as an anti-knock additive for gasoline.

GENERAL DISCUSSION OF THE BACKGROUND

Alcohols are a general class of flammable organic compounds having appreciable solubility in both aqueous (hydrophilic) and organic (hydrophobic) solvents. As a result, alcohol purification processes usually include a water-removal step. Effective water-removal steps can be expensive, energy-intensive, or otherwise inefficient, depending in part upon the alcohol involved and the degree of water-removal required.

Various lower alcohols, including methyl, ethyl and butyl alcohols, have been tried for use as a motor fuel. Use of a lower ($C_1$–$C_5$) alcohol in a blended fuel for modern internal combustion engines usually necessitates the removal of virtually all water from the alcohol used to make the alcohol-fuel blend.

Ethyl alcohol, also termed ethanol, is generally regarded as the alcohol of choice for use in formulating fuel blends. It has been known for many years that ethanol has appreciable anti-knock properties when used in a fuel mixture for internal combustion engines. In the past, ethanol was occasionally mixed with gasoline to eliminate the "knocking" experienced when only gasoline was used as a fuel. Ethanol also appears to have a synergistic affect when added to gasoline which reduces polluting emissions from the engine. As a result, several states are considering mandating use of ethanol blends as motor fuels. Such blends are popularly termed "gasohol". Gasohol typically comprises blends containing as much as 10% (v/v) ethanol in gasoline.

Unfortunately, early ethanol-fortified gasolines contained too much water. Because it is impossible to remove all the water from ethanol by simple distillation, early mixtures that were formulated by mixing "distilled" ethanol with gasoline were usually saturated with water, even at temperatures greater than normal engine operating temperature. During cooler engine operating conditions, the fuel mixture sometimes formed a separate liquid water phase which impaired engine operation. Modern engines designed for tighter motor fuel standards are simply incapable of operating with such water-containing fuel mixtures.

Modern gasohol, which contains practically no water, has not yet achieved widespread favor as a motor fuel because it is too expensive to produce relative to the prevailing costs of producing gasoline. The principal reason for such high costs is the relatively large amount of energy required to produce ethanol with sufficient yield, purity and absence of water to add to gasoline. Nevertheless, gasohol remains a viable alternative to gasoline because the ethanol fraction is a renewable resource (via fermentation) that potentially can decrease the present rate at which nonrenewable petroleum reserves are being consumed.

Much of the attention directed at producing gasohol and other liquid alternative transportation fuels from renewable sources has centered on processes that begin with fermentation. Fermentation is a process in which dilute aqueous solutions of sugars, starches readily convertible to sugars, or agricultural "waste" products containing sugars or starches are inoculated with special strains of yeast or bacteria which enzymatically convert those nutrients to carbon dioxide and ethanol. The maximum achievable concentration of ethanol in a fermentation beer is approximately 15%, with continuous processes typically producing lower concentrations. Higher ethanol concentrations from fermentation alone are not possible because an ethanol concentration greater than approximately 15% (w/w) causes death of the fermentation microorganisms. Such a low concentration of ethanol in water cannot be used as a motor fuel or fuel additive because it contains too much water. The ethanol must first be concentrated and dehydrated.

One type of gasohol production process in current use employs, after fermentation and clarification of the fermentation beer, a subsequent two-step distillation to yield "absolute", or 100%, anhydrous ethanol that can be blended with gasoline. The first distillation yields an azeotrope containing distillation is an azeotropic distillation, in which a third compound such as benzene is added to "break" the azeotrope and produce 100% ethanol. While this process effectively separates ethanol from water, it is unfortunately energy-intensive. The two distillation steps together account for more than 50% of the energy required for production of absolute ethanol from fermentation. If that energy requirement could be substantially lowered, the cost of gasohol production from fermentation would decrease and the product more widely accepted as a serious alternative to gasoline for use as a motor fuel.

Another process sometimes used for dehydration of dilute solutions of ethanol or other lower alcohol is solvent extraction, where the aqueous solution of the alcohol is mixed with a liquid organic solvent having an affinity for alcohol greater than the affinity of the alcohol for water, thereby causing a net transfer of the alcohol from the water to the organic solvent. The principal advantage of solvent extraction is that very little energy is consumed. However, in the case of ethanol, for example, no known organic solvent has an affinity for ethanol at ambient temperature that is appreciably greater than that of water. Consequently, such processes at ambient temperature require large volumes of solvent. There is also the problem of separating the ethanol from the solvent used to perform the extraction.

U.S. Pat. No. 4,490,153 (Sze and Suziu) disclosed a process by which dilute aqueous ethanol from a clarified fermentation beer is distilled ("rectified"), yielding a 90% (w/w) aqueous solution of ethanol which is extracted at low temperature (+5 to −10° F.) with a large excess volume of gasoline. The low-temperature extraction produces a gasohol blend containing approximately 10% (w/w) ethanol in gasoline and a separable liquid aqueous phase containing a small amount of ethanol and traces of gasoline. Unfortunately, that process consumes large amounts of energy in the initial distillation step where most of the water is removed. Hence, the 4,490,153 patent does not satisfy the need for a gasohol production process that consumes low amounts of energy.

Another technique is "freeze concentration" in which a solution is cooled to below its freezing point, forcing some of the solvent to freeze and increasing the concentrations of solutes remaining in the liquid phase. In U.S. Pat. No. 4,385,944, Hewitt and Tillen disclosed such a process in which a dilute aqueous solution of ethanol is added dropwise to a liquid hydrocarbon or dense gas used as a "heat-exchange liquid" at successively lower temperatures at which some of the water freezes, producing ice crystals and an ethanol-enriched liquid. The selected hydrocarbon is one that will not mix with the ethanol solution. Consequently, the ethanol-enriched solution can be separated from the hydrocarbon and from the ice crystals. However, the ethanol-enriched solution still has too much water (8 percent or more), even after multiple cycles through the Hewitt and Tillen process, to be useful as a motor fuel. No purification by solvent extraction or other process is disclosed.

Another nondistillation method of dehydrating aqueous ethanol solutions employs a solid dehydration agent or adsorbent to remove the water from the solution. The dehydration agent may be either discarded or regenerated after adsorbing the water. Examples of such adsorbents include alumina, zeolite, bauxite, fuller's earth, and acid-activated bentonite. In dehydration processes, it is usually necessary to first distill the fermentation beer to yield a distillate containing 70 to 95% (w/w) ethanol. Afterward, the distillate is contacted with a dehydration agent, producing an essentially anhydrous grade ethanol. Although the energy required for dehydration alone is less than that required for distillation, large scale production of absolute ethanol via a dehydration process usually requires a first stage distillation so that the dehydration agent does not need to remove such large volumes of water. Consequently, the dehydration method does not yield a significant energy savings over distillation.

Accordingly, there is a need for an efficient process that will extract lower alcohols from dilute aqueous solutions using a minimum amount of energy. There is also a need for an efficient method for producing an alcohol blend suitable for use as a high octane additive for motor fuel. There is also a need for such a process that is continuous. There is also a need for such a continuous process that transfers ethanol from dilute solutions formed by fermentation of renewable resources into a suitable organic solvent, the resulting solution being useful as a motor fuel additive, and the process being one that requires minimum energy and a minimal volume of extracting solvent for high recovery of ethanol from the dilute solution.

SUMMARY OF THE INVENTION

The present invention provides a new and energy-efficient process for separating lower ($C_1$-$C_5$) alcohols from aqueous solutions. The process yields either a concentrated liquid solution of the alcohol in an organic solvent or the substantially pure alcohol. Some such alcohols, such as ethanol, or organic solutions thereof are suitable for use as anti-knock additives for gasoline. Most of the water is removed from the dilute aqueous solution of the alcohol by lowering the temperature of the aqueous solution sufficiently to form ice crystals. Also, the aqueous liquid is simultaneously extracted at the same low temperature with an appropriate organic solvent. As ice crystals form, the alcohol transfers to the organic solvent, which drives the formation of more ice crystals and the further transfer of the alcohol to the organic solvent. The ice crystals can be separated from the organic solution of the alcohol by any of several known means. The organic solvent is typically an aromatic type, such as toluene, which is immiscible in aqueous solutions and has a greater affinity for the alcohol than for water. If required or desired, the organic solution of the alcohol can be distilled to enrich the concentration of the alcohol or to separate the alcohol from the organic solvent.

One object of the present invention is to provide a new and energy-efficient process for producing, from an aqueous solution of a lower alcohol, an organic solution of the alcohol containing substantially no water and a higher concentration of the alcohol than the original concentration of the alcohol in the aqueous solution.

Another object is to provide a new energy-efficient process for producing, from an aqueous solution of ethanol, a high-octane additive for gasoline, the additive consisting substantially of an enriched solution of ethanol in an aromatic solvent having appropriate anti-knock properties.

A further object is to provide a new and improved process for separating a lower alcohol from an aqueous solution of the alcohol, the process including an extraction of the alcohol using an appropriate organic solvent at a temperature sufficiently below the freezing point of water to cause at least most of the water to form into ice crystals and substantially all the alcohol to transfer into the organic solvent, optionally followed by distillation to separate the alcohol from the organic solvent.

A further object is to provide an energy-efficient process for producing a high-octane additive for gasoline, the additive consisting of an elevated concentration of ethanol in an organic solvent having appropriate anti-knock properties, the ethanol produced in dilute aqueous solutions via a fermentation process.

A further object is to provide an energy-efficient process for removing ethanol from a fermentation beer.

BRIEF DESCRIPTION OF THE DRAWINGS

The above and other features and advantages of the present invention will become more apparent from the following detailed description of the invention, which proceeds with reference to the accompanying drawings wherein.

DETAILED DESCRIPTION

The present invention is a process for separating a lower ($C_1$-$C_5$) alcohol from an aqueous solution, including a dilute aqueous solution. The process can yield either a concentrated solution of the alcohol in an organic solvent or the substantially pure alcohol, the latter via a subsequent distillation step to separate the alcohol from the organic solvent.

In the present invention, the temperature of the aqueous solution of alcohol is lowered sufficiently to cause at least a portion of the water therein to form into ice crystals, thereby increasing the concentration of the alcohol remaining in the liquid. An appropriate organic solvent at substantially the same low temperature is simultaneously added to the aqueous solution with agitation. As the ice crystals form, the alcohol transfers to the organic solvent. Eventually, substantially all the alcohol transfers to the organic solvent and substantially all the water forms into ice crystals. The ice crystals can be conveniently separated from the liquid organic solution of the alcohol by any of several known methods. If a higher concentration of the alcohol is required, a subsequent distillation of the organic solution of alcohol may be performed. This distillation would require much less energy than distillation of ethanol-water solutions.

As a specific example, we describe below the separation of ethanol from a dilute aqueous solution. The present invention applied to ethanol has appreciable value because the resulting product can be either added to gasoline to form gasohol or used as a high-octane additive for gasoline. Ethanol is an important renewable source of flammable hydrocarbon useful as a motor fuel or fuel additive. Ethanol also has many other important industrial uses.

Figure 1:
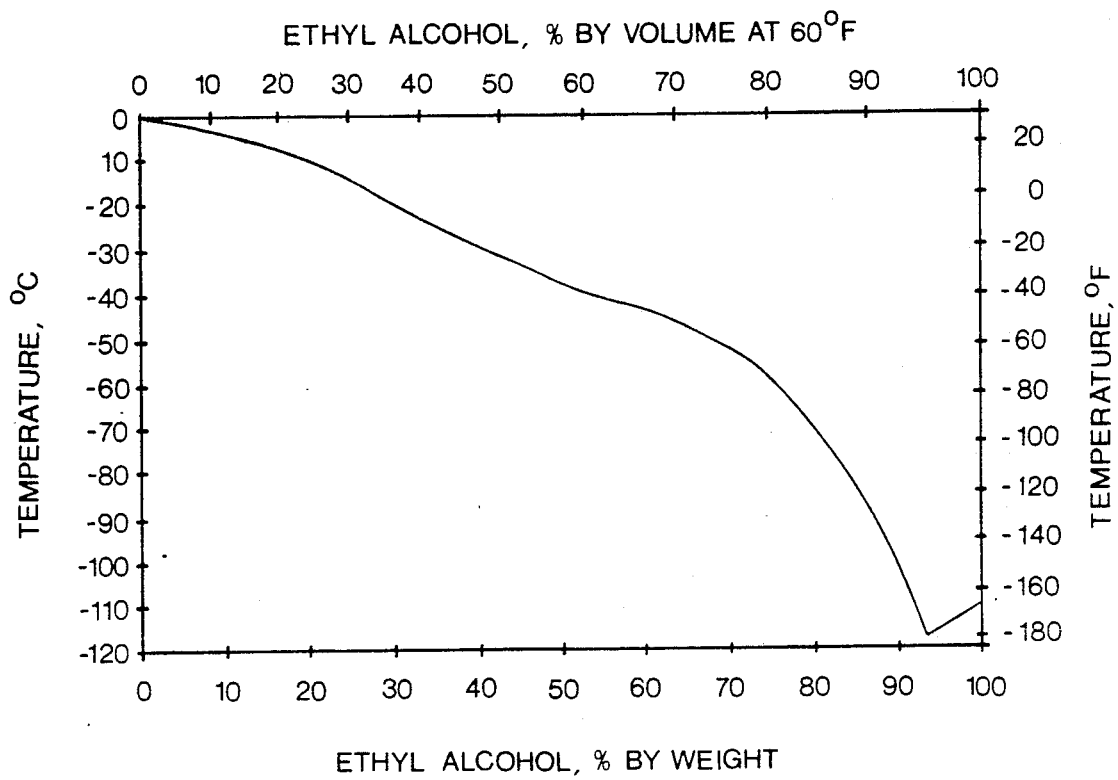
FIG. 1 is a plot of the freezing points of aqueous solutions containing various relative volumes or masses of ethanol.

FIG. 1 shows the relationship of the freezing temperature to the concentration of ethanol in an aqueous solution. It can be seen that lowering the solution temperature over a defined range increases the equilibrium concentration of ethanol in the solution. For example, at $-35°$ C., the aqueous phase contains 53% (v/v) ethanol. At $-50°$ C., the aqueous phase contains approximately 74% (v/v) ethanol at equilibrium. At $-70°$ C., the equilibrium concentration of ethanol is 84% (v/v). At $-70°$ C., all water in excess of 16% (v/v) in the solution forms into ice crystals. FIG. 1 also shows that the eutectic temperature of ethanol is $-118°$ C., at which the concentration of ethanol in solution is 95% (v/v). The eutectic temperature is the lowest melting temperature of a solution that is obtainable by varying the percentage of the components of the solution.

Figure 2:
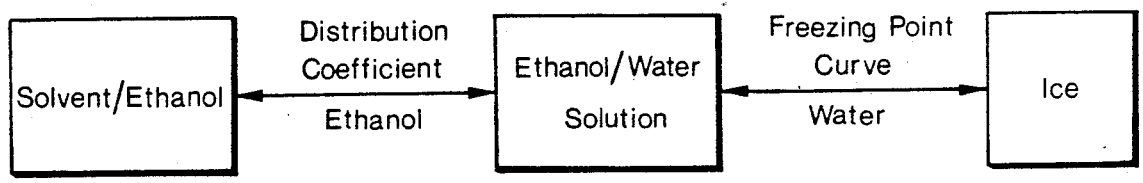
FIG. 2 is a schematic depiction of the equilibria existing when aqueous solutions of ethanol are contacted with an organic solvent at various temperatures within the range shown in FIG. 1.

All along the freezing-point curve of FIG. 1, from 0° C. to $-118°$ C., a solid-liquid equilibrium exists between solid water (ice crystals) and the ethanol-water solution, the equilibrium as shown in FIG. 2 (right half). Lowering the temperature of the solution shifts the equilibrium to the right, causing more of the water in solution to form into ice, thereby increasing the concentration of ethanol remaining in the liquid solution. At a given temperature, the concentration of ethanol in the water solution will tend to remain constant. Any removal of ethanol from the solution at subzero temperature will cause more ice to form in order to maintain the concentration of ethanol at the particular value at that temperature.

If an organic solvent immiscible in the aqueous solution is added to such a system, a perturbing force is imparted to the equilibrium shown in FIG. 2. (The best organic solvents for such purposes are those which have a greater affinity for the alcohol than for water. Such organic solvents include the aromatic solvents benzene, toluene, and xylenes). The perturbation imparted by the organic solvent is in the form of a second equilibrium (FIG. 2, left half), in which the concentrated ethanol is in equilibrium with the organic solvent. In addition, the concentrated ethanol remains in equilibrium with the water, as dictated by the distribution coefficient of the organic solvent at the prevailing temperature. As the organic solvent extracts the ethanol at subzero temperature, more ice forms, thereby maintaining the concentration of the ethanol in the water at a constant value, according to the FIG. 1 curve.

It is possible to extract virtually all the ethanol from the aqueous solution into the organic solvent. For example, if the aromatic solvent toluene is mixed with an equal volume of a 5% (v/v) ethanol solution at 25° C. in an extraction apparatus, the concentration of ethanol in the toluene will equilibrate at 0.1% (v/v). When a 5% (v/v) solution is cooled to $-70°$ C. in an extraction vessel it will produce an 84% (v/v) ethanol solution plus ice. When this 84% (v/v) solution is equilibrated with an equal volume of toluene at $-70°$ C. in the extraction apparatus, the toluene will contain as much as 44% (v/v) ethanol at equilibrium. At $-70°$ C., the toluene extracts essentially all of the ethanol leaving only ice.

If the volume of organic solvent is kept small relative to the volume of aqueous solution of ethanol, a higher concentration of ethanol in the organic solvent will be obtained after extraction. However, the total amount of ethanol recovered from the aqueous solution may be lower due to occlusion of the alcohol in dense slurries of ice crystals. A volume ratio of organic solvent to dilute aqueous solution of ethanol less than about 1:1 produces a slurry of ice that is too thick for optimal recovery of organic solvent and ethanol. Volume ratios as high as 9:1 yield maximal extraction of ethanol, but consume large volumes of organic solvent and yield a dilute organic solution of ethanol generally requiring a subsequent concentrating step such as distillation. Hence, the volume ratio may be adjusted within the range 1:1 to 9:1 to achieve the best extraction recovery of ethanol with the least practical consumption of organic solvent.

Although toluene is found to be the best solvent for extracting ethanol from an aqueous solution according to the present invention, other similar aromatic solvents, such as benzene, xylenes, or various derivatives and mixtures of benzene, toluene, and xylenes may also be satisfactorily used. Derivatives of particular suitability are those which have a substituted alkyl that has up to twenty carbons.

For example, in one test, toluene added to an equal volume of dilute aqueous ethanol solution and extracted at $-70°$ C. yielded a 44% (v/v) ethanol solution in toluene after removal of the ice crystals. A "BTX" mixture, or highly aromatic refinery stream consisting substantially of benzene, toluene, and xylenes, when added to an equal volume of dilute aqueous ethanol solution in a similar test, yielded a 27% (v/v) ethanol solution in BTX.

Use of an organic solvent other than toluene may require a temperature higher or lower than $-70°$ C. for optimal extraction of ethanol. Although the process of the present invention can be performed at any temperature between 20° C. and $-118°$ C. for ethanol, practical constraints of materials and energy consumption usually limit the extraction temperature to within the range $-50°$ C. to $-70°$ C. for extracting ethanol from a dilute aqueous solution. The colder the temperature within the range of 0° C. to $-118°$ C., the more efficient the process from a chemical perspective.

The source of ethanol in the present example is any dilute aqueous solution of the alcohol. For example, the present invention is useful for removing and concentrating ethanol from a fermentation solution. In a fermentation beer, the concentration range of ethanol is between 0 and 15% (v/v), but the usual range is between 5 and 12% (v/v). Production of ethanol from a fermentation process is amenable to a continuous process which consumes a renewable resource: namely, waste carbohydrate. After fermentation, it is usually desirable to clarify, or remove suspended solids from, the fermentation beer before performing any subsequent steps of the present invention.

Figure 3:
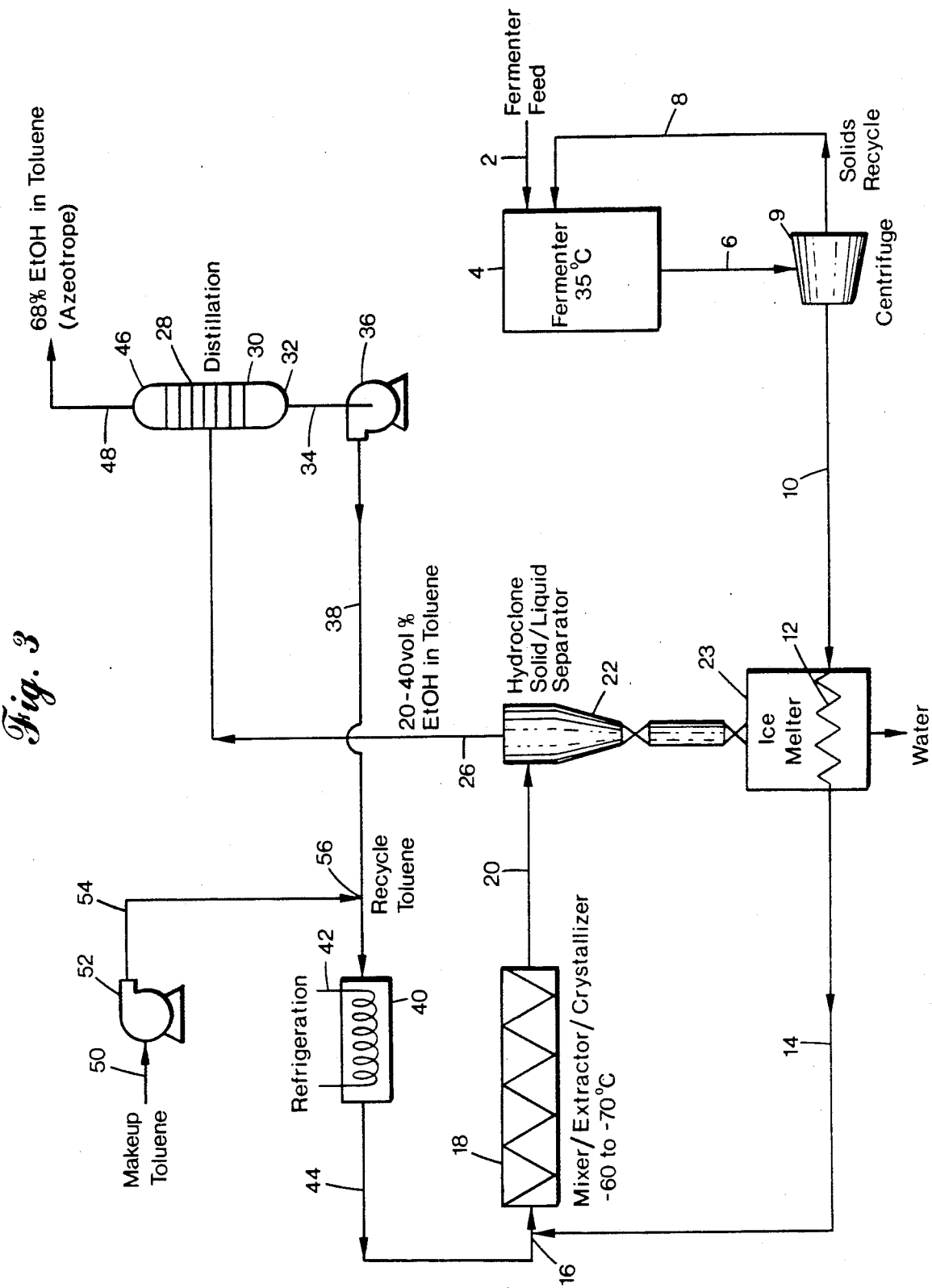
FIG. 3 is a schematic diagram of a continuous process according to the invention.

An example of a continuous process according to the present invention, in which a dilute aqueous ethanol solution is produced via fermentation, will be understood with reference to FIG. 3. The dilute aqueous solution of ethanol is produced in a fermentation vessel 4 fed by a stream 2 of an aqueous solution/suspension of carbohydrate waste, such as molasses, grains, or waste starches. Dilute aqueous ethanol solutions from other sources, however, can also be processed according to the present invention. The fermentation vessel 4 and contents thereof are maintained at approximately 35° C. or other suitable temperature, depending upon the particular microorganism used for fermentation. In a continuous process, the concentration of ethanol ranges between 0 and approximately 12% (v/v), but typically remaining at approximately 5% (v/v). The crude solution of fermentation beer is drained from the fermentation vessel 4 through a conduit 6.

The crude solution of fermentation beer from the fermentation vessel 4 is preferably clarified via a centrifuge 9 that separates suspended solids from liquid. The solids can be recycled via a conduit 8 back to the fermentation vessel 4. The clarified aqueous liquid, containing approximately 5% (v/v) ethanol, is routed via a conduit 10 to a heat exchanger 23.

The clarified 5% solution of ethanol passes through the heat exchanger 23 via a conduit 12, which contacts ice originating from a downstream process step, as described below. The heat exchanger thereby chills the 5% aqueous solution of ethanol.

The chilled 5% solution of ethanol passes through a conduit 14 and is mixed with a chilled stream of liquid toluene at a mixpoint 16 immediately before the combined liquids enter a mixer/extractor/crystallizer 18. (Although we found that toluene is the most effective solvent, any aromatic solvent selected from the group consisting of benzene, toluene, xylenes, and mixtures thereof are also effective.) The ratio at which the two chilled liquids are combined is approximately within the range 1:1 to 1:9 (ethanol solution: toluene), but the relative volume of toluene should be kept as low as possible to conserve toluene. In the mixer/extractor/crystallizer 18, the two liquids are agitated at a temperature between −50° and −70° C. Any temperature between 0° C. and −118° C. would suffice; the lower the temperature, the more chemically efficient the process. However, temperatures lower than about −70° C. are difficult to attain and maintain.

The slurry exiting the mixer/extractor/crystallizer 18 via a conduit 20 comprises an organic liquid phase consisting of 20% to 40% (v/v) ethanol in toluene, and a solid phase consisting substantially of ice crystals containing small amounts of occluded ethanol and toluene. The ice crystals are separated from the liquid phase via a centrifuge or water cyclone 22. The temperature at which the separation takes place is the same as that in the mixer/extractor/crystallizer 18. The ethanol-in-toluene solution exits the cyclone 22 through a conduit 26. The ice crystals are routed to the heat exchanger 23 to chill the clarified 5% solution of ethanol from the fermentation vessel 4.

If further concentration or purification of the ethanol is desired or required, the organic solution of ethanol can be distilled. As shown in FIG. 3, the 20-40% solution of ethanol in toluene to be distilled is routed through the conduit 26 to a still 28. In the still 28, the 20-40% ethanol-in-toluene solution is distilled to form an azeotrope comprised substantially of 68% (v/v) ethanol in toluene that escapes from the still as vapor and subsequently condensed at the still head 46. Excess toluene in the still bottoms 30 is pumped out through a conduit 34 via a pump 36, through a conduit 38, chilled by a refrigeration unit 40 to within the range −60° C. to −70° C., and returned through a conduit 34 to the mixpoint 16 upstream of the mixer/extractor/crystallizer 18. Fresh toluene is added as required through a conduit 50, a pump 52, and a conduit 54 to a mixpoint 56 immediately upstream of the refrigeration unit 40.

If further enrichment of the ethanol concentration in toluene is not required, the distillation step shown in FIG. 3 can be omitted. If no distillation is performed, the organic solution of ethanol can be collected as it exits the cyclone 22 through the conduit 26. It is possible that the organic solution exiting the cyclone 22 through the conduit 26 will still have a concentration of water, although very low, too high for the intended use of the solution. If so, the solution may be rendered anhydrous by passing it through a column packed with a dehydrating agent to remove the remaining water (not shown). Because the concentration of water in the organic solution is very low, an appropriately sized dehydration column would not require regeneration except at infrequent intervals.

The 68% ethanol-in-toluene distillate can be added directly to gasoline as an anti-knock agent. Both toluene and ethanol have an octane number greater than 100. The blending octane number of ethanol is 120, indicating that ethanol has a synergistic effect on other fuel components. The octane number of the distillate, then, should be somewhere between 110 and 120.

The above-described process for separating and concentrating ethanol from a dilute aqueous solution can also be used to separate and concentrate other lower alcohols from aqueous solutions thereof. For the purposes of this disclosure, "lower alcohol" means any alcohol that has one to five carbons and is soluble in water and in organic solvents, particularly aromatic solvents. Further, such alcohols have low pressure. (An exception is tert-butyl alcohol with a melting point of 25.6° C.) Depending upon the particular alcohol to be separated from aqueous solution, appropriate variations in temperature of ice crystallization and solvent extraction, as well as choice of particular organic solvent for extraction of the alcohol from aqueous solution, may be made within the scope of the present invention.

Having illustrated and described the principles of the invention, it should be apparent to those skilled in the art that the invention can be modified in arrangement and detail without departing from such principles. We claim all modifications coming within the spirit and scope of the following claims.

We claim:

1. A process for separating a lower alcohol from a dilute, aqueous solution of the alcohol, the process comprising:

cooling a dilute, aqueous solution of a lower ($C_1$-$C_5$) alcohol to a temperature which is sufficiently low to cause at least a portion of the water therein to freeze and which is sufficiently high that the alcohol does not solidify, thereby forming (a) a solid phase primarily comprising ice crystals and (b) an aqueous liquid phase containing an elevated concentration of the alcohol;

solvent-extracting the alcohol from the aqueous liquid phase at substantially the same low temperature by adding an organic solvent, in which the lower alcohol is soluble, to the aqueous liquid phase and agitating the resulting mixture, the organic solvent being substantially immiscible in the aqueous liquid at such low temperature, thereby effecting a net transfer of the alcohol from the aqueous liquid phase to the organic solvent and causing at least some of the remaining water to form ice crystals; and separating the organic solvent containing the alcohol from the solid phase while still at such a lower temperature.

2. A process according to claim 1 wherein the lower alcohol is selected from the group of alcohols having one to five carbon atoms that consists of methanol, ethanol, propanols, butanols, and pentanols.

3. A process according to claim 1 further comprising conducting the solvent-extracting using an organic solvent that has a greater affinity for the lower alcohol than for water.

4. A process according to claim 1 wherein the organic solvent comprises at least one aromatic liquid solvent.

5. A process according to claim 4 wherein the aromatic liquid solvent is selected from the group consisting of benzene, toluene, xylenes, derivatives thereof having a substituted alkyl that has up to twenty carbons, and mixtures thereof.

6. A process according to claim 1 wherein the forming of ice crystals and solvent-extracting the alcohol from the remaining aqueous liquid phase occur simultaneously.

7. A process according to claim 1 wherein the low temperature is within the range of 0° C. to the eutectic temperature of the aqueous alcohol solution, the eutectic temperature being less than 0° C.

8. A process according to claim 1 further comprising distilling the organic solution of the alcohol after removing the ice crystals therefrom, the distillation producing a distillate having at least a higher concentration of the alcohol than the concentration of the alcohol in the organic solution before distillation.

9. A process according to claim 8 further comprising conducting the distilling under conditions that produce a fraction in which the alcohol is substantially pure.

10. A process for producing an additive for gasoline, the process comprising:

cooling a dilute, aqueous solution of ethanol to a temperature which is sufficiently low to cause at least a portion of the water therein to freeze and which is sufficiently high that the alcohol does not solidify, thereby forming (a) a solid phase primarily comprising ice crystals and (b) an aqueous liquid phase containing an elevated concentration of ethanol;

solvent-extracting the ethanol from the aqueous liquid phase at substantially the same low temperature by adding an organic solvent, in which ethanol is soluble, to the aqueous liquid phase and agitating the resulting mixture, the organic solvent being substantially immiscible in the aqueous liquid and having an appropriate octane number for use as a motor fuel additive for internal combustion engines, thereby effecting a net transfer of ethanol from the aqueous liquid phase to the organic solvent to provide an organic solution of ethanol and causing substantially all of the remaining water to form ice crystals; and separating the organic solution of ethanol from the solid phase while still at such a low temperature.

11. A process according to claim 10 further comprising conducting the solvent-extracting using an organic solvent that has a greater affinity for the lower alcohol than for water.

12. A process according to claim 10 wherein the organic solvent comprises at least one aromatic liquid solvent.

13. A process according to claim 10 wherein the organic solvent comprises at least one aromatic liquid solvent selected from the group consisting of benzene, toluene, xylenes, derivatives thereof having a substituted alkyl group that has up to twenty carbons, and mixtures thereof.

14. A process according to claim 10 wherein the low-temperature steps of forming ice crystals and solvent-extracting the ethanol from the aqueous liquid phase occur simultaneously.

15. A process according to claim 10 wherein the low temperature is within the range of 0° C. to the eutectic temperature of an aqueous ethanol solution.

16. A process according to claim 15 wherein the temperature is from −50° C. to about −118° C.

17. A process according to claim 16 wherein the temperature is about −70° C.

18. The process according to claim 10 further comprising the step of distilling the organic solution of ethanol, after removing the ice crystals therefrom, the distillation yielding a distillate with at least a higher concentration of ethanol than the ethanol concentration in the aromatic solvent before distillation.

19. A process for producing a high-octane additive for gasoline, the process comprising:

fermenting a carbohydrate-containing liquor to produce a dilute aqueous ethanol solution;

removing solids from the dilute aqueous ethanol solution;

cooling the aqueous ethanol solution to a temperature which is sufficiently low to cause at least a portion of the water therein to freeze and which is sufficiently high that the alcohol does not solidify, thereby forming (a) a solid phase primarily comprising ice crystals and (b) an aqueous liquid phase containing an elevated concentration of ethanol;

solvent-extracting the ethanol from the aqueous liquid phase at substantially the same low temperature by adding an organic solvent, in which ethanol is soluble, to the aqueous liquid phase and agitating the resulting mixture, the organic solvent being substantially immiscible in the aqueous liquid and having an appropriate octane number for use as a motor fuel additive for internal combustion engines, thereby effecting a net transfer of ethanol from the aqueous liquid phase to the organic solvent to provide an organic solution of ethanol and causing substantially all of the remaining water to form ice crystals; and separating the organic solution of ethanol from the solid phase while still at such a low temperature.

20. A process according to claim 19 further comprising distilling the organic solution of the alcohol after removing the ice crystals therefrom, the distillation producing a distillate having at least a higher concentration of the alcohol than the concentration of the alcohol in the organic solution before distillation.

21. A process according to claim 1 wherein the dilute, aqueous solution comprises less than 15 vol. % lower alcohol.

22. A process according to claim 10 wherein the dilute, aqueous solution comprises less than 15 vol. % ethanol.

23. A process according to claim 19 wherein the dilute aqueous ethanol solution comprises less than 15 vol. % ethanol.

* * * * *

UNITED STATES PATENT AND TRADEMARK OFFICE
CERTIFICATE OF CORRECTION

PATENT NO. : 5,028,240

DATED : July 2, 1991

INVENTOR(S) : Raymond H. Moore et al.

It is certified that error appears in the above-identified patent and that said Letters Patent is hereby corrected as shown below:

Column 2, line 25, after "containing" insert --a maximum of 95% ethanol in water. The second--;

Column 6, line 53, "20°C. and -118°C." should be --0°C. and --118°C.--;

Column 8, line 44, after "Further, such alcohols have low" insert --melting points, generally below -80°C at atmospheric--.

Signed and Sealed this

Thirteenth Day of April, 1993

*Attest:*

STEPHEN G. KUNIN

*Attesting Officer*  *Acting Commissioner of Patents and Trademarks*